United States Patent [19]

Diehl et al.

[11] Patent Number: 4,963,184

[45] Date of Patent: Oct. 16, 1990

[54] TOOTH FILLING MATERIAL AND METHOD OF ITS PREPARATION

[75] Inventors: Walter Diehl, Hanau; Hans-Martin Ringelstein, Frankfurt, both of Fed. Rep. of Germany

[73] Assignee: Degussa Aktiengesellschaft, Frankfurt am Main, Fed. Rep. of Germany

[21] Appl. No.: 365,294

[22] Filed: Jun. 13, 1989

[30] Foreign Application Priority Data

Jun. 22, 1988 [DE]  Fed. Rep. of Germany ....... 3820970

[51] Int. Cl.$^5$ ........................... C22C 29/14; B22F 5/00
[52] U.S. Cl. ........................ 75/247; 106/35; 419/2; 433/226; 433/228.1
[58] Field of Search ............... 433/226, 228.1; 106/35; 75/246, 247; 419/2

[56] References Cited

U.S. PATENT DOCUMENTS

| | | | |
|---|---|---|---|
| 2,040,179 | 5/1936 | Livingstone | 433/226 |
| 3,667,934 | 6/1972 | Ingersoll | 433/226 |
| 4,634,383 | 1/1987 | Beyer et al. | 433/226 |

FOREIGN PATENT DOCUMENTS 3042008  6/1982  Fed. Rep. of Germany .

*Primary Examiner*—Brooks H. Hunt
*Assistant Examiner*—Ngoclan T. Mai
*Attorney, Agent, or Firm*—Beveridge, DeGrandi & Weilacher

[57] ABSTRACT

A meterial well-suited for gold fillings in tooth cavities consists of a porous sintered compact which is prepared from platelet-shaped gold powder produced by chemical precipitation and which exhibits a pore volume of 80 to 90%.

8 Claims, No Drawings

TOOTH FILLING MATERIAL AND METHOD OF ITS PREPARATION

INTRODUCTION AND BACKGROUND

The present invention relates to a tooth filling material formed of a porous sintered gold compact body to be used for filling cavities and which are solidified under the action of ultrasound.

A number of metallic filling substances are known in the field of preservation dentistry such as e.g. amalgams and cast alloys in the form of inlays or filler gold. The filling of dental cavities with filler gold is one of the oldest tooth filling methods. Chemically pure gold in the form of gold foil, gold sponge or gold powder is used for these gold plug fillings.

Gold plug fillings prepared from pure gold are highly regarded with respect to durability, esthetics and corrosion resistance. However, significant disadvantages of gold plug fillings are the technically complicated and time-consuming preparation of the cavity and the positioning of the filling, which also requires great skill. Thus, a very meticulous working of the cavity is necessary at first with undercuts and a roughening of the cavity walls which can not be performed automatically. Both procedures are absolute prerequisites for a sufficient adhesion of the gold in the cavity. Moreover, the cavity must be absolutely free of moisture during the gold filling procedure. This applies not only to the saliva flow but also to the respiratory air of the patient. This necessitates the use of so-called cofferdam foils, which is likewise time-consuming and occasionally very unpleasant for the patient. In addition, the material of the gold plug filling must be annealed in a very clean alcohol flame immediately before being placed into the cavity in order that all impurities on the surface are removed and a cohesive bond between the individual gold particles is achieved. The ability of the gold to be cold-welded, the basis of gold plug filling, is sharply reduced by a contamination of the surface, especially by liquid or moisture films.

German Patent No. 30 42 008 teaches a gold filling method in which a porous sintered compact or a skein of gauze wire, preferably of gold, is introduced into the cavity together with a plastic or liquid organic binder which solidifies in a temperature range from 15 to 40° C. Binders such as methyl methacrylate or other plastics or dental cements customarily employed in dentistry are mentioned. The resulting composition is then manipulated with manual tamping devices into the cavity and then solidified. The sintered gold compacts formed thereby exhibit a pore volume of 58 to 66%. However, surfaces can not be produced with this method that are free of all objectionable factors. In addition, these surfaces are not purely metallic but still contain the organic binder, usually methacrylates.

U.S. Pat. No. 1,040,972 teaches a plastic gold material consisting of gold fibers or gold sponge impregnated with a wax which softens under heat and hardens during cooling, which material can also be used to prepare dental fillings. Here as well, surfaces cannot be produced that are completely satisfactory since the wax remains in the dental filling.

German Patent No. 34 03 779 teaches a tooth filling material to be placed in cavities and solidified under the action of ultrasound which consists of platelet-shaped gold powder and polyethylene glycol in amounts of 0.5 to 5% by weight. The presence of an organic binder in the dental filling represents a disadvantageous in this patented development.

SUMMARY OF THE INVENTION

An object of the present invention is to provide a tooth filling material of a porous sintered gold compact adapted to be placed in cavities and solidified under the action of ultrasound which tooth filling material does not require the use of organic binders.

In achieving the above and other objects, the present invention features a sintered compact formed of platelet-shaped gold powder prepared by chemical precipitation and exhibiting a pore volume of 80 to 90%.

The sintered compact preferably exhibits a strip form.

This tooth filling material is advantageously prepared in such a manner that platelet-shaped gold powder prepared by chemical precipitation is sintered without compressive prepressing at 300 to 900° C. to a porous form body compact with a pore volume of 80 to 90%.

The gold platelets preferably exhibit a size of 5 to 100 μm at a thickness of 0.1 to 5 μm.

It is also advantageous if the sintering of the gold platelets is performed 15 to 45 minutes at 500 to 700° C., especially at 550 to 640° C.

Surprisingly, gold plug fillings can be prepared with these sintered compacts under the action of ultrasound which exhibit a good durability and a pure metallic surface. In addition, these sintered compacts exhibit a mechanical consistency which permits the material to be smoothly introduced and shorn off in the cavity.

DETAILED DESCRIPTION OF THE INVENTION

The preparation of these sintered compacts takes place in such a manner that a platelet-shaped gold powder prepared according to a known method by chemical precipitation is sintered in a loose pile without precompression in a suitable form at temperatures of 300 to 900° C. A porous gold shaped body is produced thereby in the form and must exhibit a pore volume of 80 to 90%. If mechanically prepared gold platelets are used, the sintered compact is not suitable for the filling of tooth cavities.

The following example is intended to illustrate the invention in more detail:

Platelet-shaped gold powder of an average particle size of $15 \times 0.3$ μm$^2$ was precipitated from a hydrochloric size of 15 x 0.3 μm acid solution of gold salt in the presence of protective colloids by means of reduction with an unsaturated alcohol. This gold powder was distributed into a groove open at the top and with a rectangular cross section ($30 \times 1.5 \times 0.3$ mm$^3$) and sintered 30 minutes at 600° C. in the air. The strip produced in this manner exhibited a pore volume of 83% and was gradually introduced into a tooth cavity, where the material was compressed and solidified with an ultrasound tool (f=40 kHz) with a contact pressure of 3 to 5 N. The finished tooth filling exhibited a shearing resistance of 60 N . mm$^{-2}$ The following is an improved method for obtaining small platelets of gold powder:

A solution of 3.3 kg of HAuCl$_4$ with about 33% Au is set to a pH of 0.5-1 with a diluted soda brine and then converted with a 2 kg aqueous 30% gum arabic solution. At a maximum temperature of 30-35° C., there is introduced with stirring over a time period of about 90 minutes, 1 liter of allylalcohol. The reaction mixture is held at room temperature until the appearance of the first gold flake. Then, it is heated to 60–70° C. and held at that temperature for about 15 minutes. The gold powder is decanted, washed with water and alcohol, and is subjected to suction and thereafter dried at 70° C. There is obtained in quantitative yield crystalline platelets with a particle size of less than or equal to 25μm.

The gold platelets can also be formed by other means such as milling of pellets of gold powder.

Protective colloids that can be used in addition to gum arabic are dextrin, methyl cellulose or tannic acid. As reduction agents all unsaturated alcohols can be used, such as allylalcohol or propargylalcohols or endioles.

Further variations and modifications will be apparent to those skilled in the art from the foregoing and are intended to be encompassed by the appended claims.

German P No. 38 20 970.5 is incorporated herein by reference.

We claim:

1. A tooth filling material comprising a porous sintered gold compact adapted to be placed in cavities and solidified under the action of ultrasound, formed of platelet-shaped gold powder prepared by chemical precipitation without compressive prepressing and exhibits a pore volume of 80 to 90%.

2. The tooth filling material according to claim 1, wherein the sintered compact is in the form of a strip.

3. A tooth filling material comprising a porous sintered gold compact adapted to be placed in cavities and solidified under the action of ultrasound, formed of platelet-shaped gold powder produced by chemical precipitation and sintering said powder without compressive prepressing at 300 to 900° C. to form a porous body with a pore volume of 80 to 90°%.

4. The tooth filling material according to claim 3, wherein the gold platelets exhibit a size of 5 to 100 μm at a thickness of 0.1 to 5 μm.

5. The tooth filling material according to claim 3, wherein gold platelets are precipitated from an acid solution in the presence of a protective colloid.

6. A method of preparing tooth filling material which is a porous sintered gold compact comprising providing platelet-shaped gold powder produced by chemical precipitation, and sintering said powder without compressive prepressing at 300 to 900° C. to form a porous body with a pore volume of 80 to 90%.

7. The method according to claim 6, wherein the gold platelets exhibit a size of 5 to 100 μm at a thickness of 0.1 to 5 μm.

8. The method according to claim 6 wherein the sintering of the gold platelets is performed for 15 to 45 minutes at 500 to 700° C.

* * * * *